US006465441B2

(12) United States Patent
Pelleg et al.

(10) Patent No.: US 6,465,441 B2
(45) Date of Patent: Oct. 15, 2002

(54) SCREENING METHOD FOR MODULATION OF HUMAN MAST CELL ACTIVATION

(75) Inventors: Amir Pelleg, Haverford, PA (US); Edward S. Schulman, Philadelphia, PA (US)

(73) Assignee: Duska Scientific Co., Haverford, PA (US)

( * ) Notice: Subject to any disclaimer, the term of this patent is extended or adjusted under 35 U.S.C. 154(b) by 0 days.

(21) Appl. No.: 10/027,052

(22) Filed: Dec. 20, 2001

(65) Prior Publication Data

US 2002/0055515 A1 May 9, 2002

Related U.S. Application Data

(62) Division of application No. 09/381,692, filed as application No. PCT/US98/05922 on Mar. 24, 1998, now Pat. No. 6,372,724.
(60) Provisional application No. 60/041,461, filed on Mar. 25, 1997.

(51) Int. Cl.⁷ .................. A61K 31/70; A61K 31/52; C12Q 1/00; G01N 33/53; G01N 33/567
(52) U.S. Cl. .................. 514/47; 514/48; 514/263.1; 435/7.2; 435/4
(58) Field of Search .................. 536/26.23, 27, 536/28; 514/47, 48, 263.1; 435/7.2, 4

(56) References Cited

U.S. PATENT DOCUMENTS

| 4,185,119 A | 1/1980 | Kikuchi | 424/258 |
|---|---|---|---|
| 5,733,916 A | 3/1998 | Neely | 514/262 |
| 5,874,420 A | 2/1999 | Pelleg | 514/81 |
| 6,372,724 B1 * | 4/2002 | Pelleg et al. | 514/47 |

OTHER PUBLICATIONS

Bennett et al., "Rat Mast Cells Permeabilized With ATP Secrete Histamine In Response To Calcium Ions Buffered In The Micromolar Range", *J. Physiol*, 317:335–345 (1981).
Boyer et al., "Identification of Competitive Antagonists of the $P2Y_1$ Receptor", *Molecular Pharmacology*, 50:1323–1329 (1996).
Nirmal Chakravarty, "The role of Plasma Membrane $Ca^{++}$–$Mg^{++}$ Activated Adenosine Triphosphatase of Rat Mast Cells on Histamine Release", *Acta pharmacol. et toxicol*, 47:223–235 (1980).
Shamshad Cockcroft and Bastien D. Gomperts, "The $ATP^{4-}$ Receptor of Rat Mast Cells", *Biochem. J.*, 188:789–798 (1980).
S. Crockcroft and B. D. Gomperts, "Activation And Inhibition Of Calcium–Dependent Histamine Secretion By ATP Ions Applied to Rat Mast Cells", *J. Physiol.*, 296:229–243 (1979).
S. Crockcroft and B. D. Gomperts, "ATP induces nucleotide permeability in rat mast cells", *Nature*, 279:541–542 (1979).

Bertil Diamant, "The Effects of Compound 48/80 and Distilled Water on the Adenosine Triphosphate Content of Isolated Rat Mast Cells", *Acta physiol. scand.*, 71:283–290 (1967).
Tatham et al., "Characterisation of the $ATP^{4-}$ receptor that mediates permeabilisation of rat mast cells", *European Journal of Pharmacology*, 147:13–21 (1988).
Peter E. R. Tatham and Manfred Lindau, "ATP–induced Pore Formation in the Plasma Membrane of Rat Peritoneal Mast Cells", *The Journal of General Physiology*, 95:459–476 (1990).
Simon et al., "Characterisation of a recombinant $P_{2y}$ purinoceptor", *European Journal of Pharmacology—Molecular Pharmacology Section*, 291:281–289 (1995).
Pelligrino et al., "Lung mechanics during induced bronchoconstriction", *American Physiological Society*, (1996).
Saito et al., "Extracellular ATP Stimulates Interleukin–Dependent Culture Mast Cells and Eosinophils through Calcium Mobilization", *Int. Arch Allergy Appl. Immunol.*, 94:68–70 (1991).
Yuri Osipchuk and Michael Cahalan, "Cell–to–cell spread of calcium signals mediated by ATP receptors in mast cells" *Nature*, 359: 241–244 (1992).
Schulman et al., "ATP Modulates Histamine Release from Human Lung Mast Cells", *American Journal of Respiratory and Critical Care Medicine*, 155(4), Part 2: A619 (Apr. 1997).
Schulman et al. "ATP Modulates Anti–IgE–Induced Release of Histamine from Human Lung Mast Cells", *The Journal of Allergy and Clinical Immunology, American Academy of Allergy Asthma & Immunology*, 101(1)Part 2: S209 (Jan. 1998).
B. Diamant, "The Influence of Adenosine Triphosphate on Isolated Rat Peritoneal Mast Cells", *Int. Arch. Allergy*, 36:3–21 (1969).
Keiji Izushi and Kenji Tasaka, "Essential Role of ATP and Possibility of Activation of Protein Kinase C in $Ca^{2+}$–Dependent Histamine Release from Permeabilized Rat Peritoneal Mast Cells", *Pharmacology*, 42:297–308 (1991).
R. Keller, *Tissue Mast Cells In Immune Reactions*, S. Karger, New York, NY pp. 38–39 (1966).

(List continued on next page.)

Primary Examiner—Zohreh Fay
Assistant Examiner—Brian-Yong Kwon
(74) Attorney, Agent, or Firm—Drinker Biddle & Reath LLP

(57) ABSTRACT

Human mast cell activation is modulated by ATP binding to P2-purinoceptors on the mast cell surface. ATP binding to the purinoceptors provides a target for therapeutic intervention for the treatment of disorders characterized by undesireable mast cell mediator release, such as asthma and allergy. Inhibitors of ATP binding to mast cell P2-purinoceptors are useful therapeutic agents for treatments of those disorders. Methods of treatment using agents, and in vitro screening assays for selection of the therapeutic agents, are described.

11 Claims, 6 Drawing Sheets

OTHER PUBLICATIONS

Sudo et al., "Extracellular ATP Activates Mast Cells Via a Mechanism That is Different from the Activation Induced by the Cross–Linking of Fc Receptors", *The Journal of Immunology,* 3970–3979 (1996).

Katsumi Sugiyama, "Calcium–dependent Histamine Release With Degranulation From Isolated Rat Mast Cells By Adenosine 5'–Triphosphate", *Japan J. Pharmacol.,* 21:209–226 (1971).

Qian Y–X and McCloskey MA (1993) "Activation of Mast Cell K+ Channels Through Multiple G Protein–Linked Receptors," Proc. Natl. Acad. Sci. USA 90: 7844–7848.

Schulman et al., "P2–Purinoceptor–Mediated Enhancement of Anti–IGE–Stimulated Human Lung Mast Cell Histamine Release", *Drug Dev. Res.,* 43:40 (Jan. 1998).

Schulman et al., "Mechanisms of ATP's enhancement of histamine release from human lung mast cells (HLMC)", *Am. J. Res. Crit. Care Med.,* 157:A397 (Mar. 1998).

Z.H. Jattar and F.L. Pearce, "Histamine secretion from mast cells stimulated with ATP", *Agents and Actions,* 30:64–66 (1990).

Nirmal Chakravarty, "The Role of Plasma Membrane $Ca^{++}$–$Mg^{++}$ Activated Adenosine Triphosphatase of Rat Mast Cells on Histamine Release", *Acta Pharmacol. et toxicol.,* 47: 223–235 (1980).

\* cited by examiner

HLMC

SCREENING METHOD FOR MODULATION OF HUMAN MAST CELL ACTIVATION

CROSS-REFERENCE TO RELATED APPLICATION

This application is a divisional of U.S. application Ser. No. 09/381,692, filed Dec. 2, 1999, patented U.S. Pat. No. 6,372,724 B1, which is a 371 of PCT/US98/05922, filed Mar. 24, 1998, abandoned, which claimed priority from U.S. provisional patent application No. 60/041,461, filed Mar. 25, 1997, abandoned.

REFERENCE TO GOVERNMENT GRANT

The invention was supported in part by grant AI 20634 from the National Institutes of Health. The United States government has certain rights in the invention.

FIELD OF THE INVENTION

The invention relates to the modulation of human mast cell activation by compounds which modulate adenosine 5'-triphosphate (ATP) binding to ATP receptors (P2-purinoceptors) on the cells. The invention further relates to the treatment of disorders characterized by undesirable mediator release from stimulated mast cells, particularly immunologically stimulated lung mast cells. The invention also relates to methods for in vitro screening of candidate therapeutic agents for treating such disorders.

BACKGROUND OF THE INVENTION

Mast Cells

Mast cells comprise a normal component of the connective tissue that plays an important role in immediate (type I) hypersensitivity and inflammatory reactions by secreting a large variety of chemical mediators from storage sites in their granules upon stimulation. Mast cells, and their circulating counterparts the basophils, possess surface receptors known as FcεRI. The receptors are specific for antibody ε heavy chains.

The event that initiates immediate hypersensitivity is the binding of antigen to IgE on the mast cell or basophil surface. Both cell types are activated by cross-linking of FcεRI molecules, which is thought to occur by binding multivalent antigens to the attached IgE molecules.

Mast cells may also be activated by mechanisms other than cross-linking FcεRI, such as in response to mononuclear phagocyte-derived chemocytokines, to T cell-derived cytokines and to complement-derived anaphylatoxins. Mast cells may also be recruited and activated by other inflammatory cells or by neurotransmitters which serves as links to the nervous system.

When antigen binds to IgE molecules attached to the surface of mast cells, a variety of mediators are released which give rise to increased vascular permeation, vasodilation, bronchial and visceral smooth muscle contraction, and local inflammation. In the most extreme form of immediate hypersensitivity reaction known as anaphylaxis, mediators released from mast cells can restrict airways to the point of asphyxiation. So-called atopic individuals, who are prone to develop strong immediate hypersensitivity responses, may suffer from asthma, hay fever or chronic eczema. These individuals possess higher than average plasma IgE levels.

Antigens that elicit strong immediate hypersensitivity reactions are known as allergens. Allergy afflicts twenty percent of the United States population.

Immediate hypersensitivity results from the following sequence of events: production of IgE by B cells in response to antigen, binding of the IgE to FcεRI on the surface of mast cells, interaction of re-introduced antigen with the bound IgE and activation of the mast cells and release of mediators. Antigen binding can be simulated by polyvalent anti-IgE or by anti-FcεRI antibodies. Such antibodies can activate mast cells from atopic as well as non-atopic individuals, whereas allergens activate mast cells only in atopic persons.

Mediators released from mast cells may be divided into two broad classes, pre-formed or secretory granule associated mediators and nonpreformed or newly synthesized mediators. The pre-formed mediators include biogenic amines, most notably histamine. The pre-formed mediators also comprise granule macromolecules such as proteoglycans, most notably heparin and chondroitin sulfate E; chemotactic factors such as eosinophil and neutrophil chemotactic factors of anaphylaxis; and enzymes such as proteases, tryptase, chymase, cathepsin G-like enzyme, elastase, carboxypeptidase A and acid hydrolases. The non-preformed mediators include products of arachidonic acid, prostaglandin $D_2$, leukotrienes $C_4$ and $B_4$ and platelet activating factor. Another class of mediators, the cytokines, are produced by mast cells upon IgE-mediated activation, or by other cells, including recruited $T_H2$ lymphocytes. The cytokines are predominantly responsible for the late phase reaction which begins two to four hours after elicitation of many immediate hypersensitivity reactions. One cytokine, tumor necrosis factor alpha, may exist in the mast cells as pre-formed stores, or may represent a newly synthesized product released over a period of hours.

Mediators released from human mast cells are central to the pathophysiology of allergy, asthma and anaphylaxis. In particular, mast cells and their release of histamine and other mediators play an important role in the symptomatology of asthma and other human diseases. During the early phase of human lung hypersensitivity reactions upon exposure to antigen (i.e., pollens, cats, etc.), mast cells release and are the major source of histamine, and newly synthesized lipid products of arachidonic acid metabolism: prostaglandin $D_2$ and leukotriene $C_4$. These mediators produce immediate breathlessness, which subsides in one hour but returns within 2–4 hours (the "late phase" response). Attesting to their primal role in hypersensitivity responses, human lung mast cells (HLMC) are characterized by mRNA generation, protein synthesis and release of so-called $T_H2$ cytokines within these first few hours of activation. These cytokines including IL-5, and IL-13 are believed to be central to the evolution of chronic allergic/asthmatic states. In the lung, only mast cells are a source of histamine. Thus, histamine release is a distinct marker of mast cell activation and behavior. For a review of the role of mast cells in inflammatory responses in the lung, see Schulman, *Critical Reviews in Immunology*, 13(1):35–70 (1993), the entire disclosure of which is incorporated herein by reference.

Clinically, asthma is recognized by airway hyperactivity and reversible airways obstruction. Pathological derangements at the tissue level include constriction of airway smooth muscle, increased vascular permeability resulting in edema of airways, outpouring of mucus from goblet cells and mucus glands, parasympathetic nervous system activation, denudation of airway epithelial lining cells, and influx of inflammatory cells. Underlying these tissue effects are direct effects of potent mediators secreted following physical, inflammatory, or immunological activation and degranulation. The early phase of the asthmatic reaction is mediated by histamine and other mast cell mediators that induce rapid effects on target organs, particularly smooth muscle. The pathophysiologic sequence of asthma may be initiated by mast cell activation in response to allergen binding to IgE. Evidence exists to link exercise-induced asthma and so-called "aspirin-sensitive" asthma to HLMC degranulation.

Pharmacologic Modulation of Mast Cell Function

A limited number of pharmacologic agents have been tested for effect on HLMC activation-secretion. The beta-adrenergic agonist pharmacologic agents, as typified by fenoterol, are the most potent global inhibitors of HLMC. Though widely touted as "mast cell stabilizers," disodium cromoglycate and nedocromil sodium poorly inhibit purified HLMC histamine release. While certain corticosteroids have been found to suppress IgE-mediated generation of late-phase cytokine mRNA and protein (e.g., IL-5), release of early phase mediators (e.g., histamine and $LTC_4$) are unaffected by corticosteroids. HLMC release has been shown to be inhibited by the immunosuppressant agents FK-506, cyclosporin A and auranofin. Arachidonate pathway inhibitors are of considerable importance, they may leave the release of other allergic mediators (e.g., histamine, proteases) unaffected. Such arachidonate pathway inhibitors include inhibitors of 5-lipoxygenase and inhibitors of cyclooxygenase.

Adenosine and Adenosine Triphosphate

ATP is found in every cell of the human body; it plays a major role in cellular metabolism and energetics. ATP is released into the extracellular fluid under physiologic and pathophysiologic conditions. For example, ATP is released from ischemic cells, activated platelets, apoptotic and necrotic cells, nerve terminals as a co-transmitter, and muscle fibers during exercise. Inhalation of aerosolized ATP has been shown to trigger bronchoconstriction in healthy and asthmatic human subjects (Pellegrino et al., *J. Appl. Physiol.* 81, 964–975, 1996). Once outside cells, ATP exerts different actions in various tissues and organs. These actions are mediated by distinct cell surface receptors, termed P2-purinoceptors. These receptors are different from the adenosine receptors, termed P1-purinoceptors. This distinction of different receptors is critical, as adenosine is a breakdown product of ATP. The P2-purinoceptors comprise two major families, P2X and P2Y. Each family consists of at least seven members ($X_{1-7}$ and $Y_{1-7}$). The P2X family represents cell membrane ligand-binding ion channels permeable to $Na^+$, $K^+$, and $Ca^{2+}$. The P2Y-purinoceptors constitute G-protein-linked receptors, often coupled to phospholipase C and, hence, to inositol triphosphate formation. There are at least seven different subclasses of P2Y receptor, based upon agonist potency profiles. For a description of the various P2Y subtypes, see Abbrachio and Burnstock, *Pharmac. Ther.* 64, 445–475, 1994, the entire disclosure of which is incorporated herein by reference.

ATP has been shown to induce histamine release from rat peritoneal mast cells (Keller, *Tissue Mast Cells In Immune Reactions*, S. Karger, p. 38–39, 1966; Diamant, *Int. Arch. Allergy* 36:3–21, 1969; Sugiyama, *Japan. J. Pharmacol.* 21, 209–226, 1971; Cockcroft and Gomperts, *J. Physiol* 296, 229–243, 1979). One study attempted to identify the receptor which mediates the action of ATP on rat mast cells (Tatham et al., *Euro. J. Pharmacol* 147, 13–21, 1988). It was concluded in the study that the receptor is actually stimulated by a minor component of ATP, termed $ATP^{4-}$ (Id.). $ATP^{4-}$ effects are mediated through activation of the $P2X_7$-purinoceptor (previously termed the P2Z-purinoceptor) expressed on the rat mast cell surface (Bennett et al., *J. Physiol.* (Lond.) 317:335–345, 1981).

While rat studies suggest that ATP can directly induce mediator release from lung mast cells, these results cannot necessarily be applied to human mast cells, as will be apparent from the following disclosure.

SUMMARY OF THE INVENTION

A method for inhibiting mediator release from stimulated human mast cells is provided. Human mast cells are contacted with an effective amount of an agent which inhibits ATP binding to P2-purinoceptors on the cells. Preferably, the agent inhibits ATP binding to a P2Y-purinoceptor on the cells, most preferably the $P2Y_1$- or $P2Y_2$-purinoceptor. The agent may comprise, for example, a P2Y-purinoceptor antagonist or an allosteric modifier of a P2Y-purinoceptor.

According to one embodiment of the invention, the stimulated mast cells so treated are mast cells which comprise immunologically stimulated mast cells. While the mast cells may be derived from any human tissue, the invention is most advantageously practiced on lung, gut or joint mast cells.

According to another embodiment, the invention is a method for treating a human subject for a disorder characterized by undesirable release of mediator from immunologically stimulated lung mast cells. An effective amount of an agent which inhibits ATP binding to P2-purinoceptors on mast cells is administered to the subject. The disorder may, for example, be a disorder characterized by the undesirable release of histamine, such as allergy or asthma. The disorder may also comprise inflammatory lung disease, or bronchoconstriction, such as bronchoconstriction associated with pulmonary embolism.

According to one particularly preferred embodiment of the invention, a human subject is treated for a bronchoconstriction caused by histamine release from stimulated lung mast cells by administration of an effective amount of an agent which inhibits ATP binding to a P2-purinoceptor, preferably to a P2Y-purinoceptor, most preferably the $P2Y_1$- or $P2Y_2$-purinoceptor, on lung mast cells.

The invention also provides a method for selecting agents useful for inhibiting mediator release from stimulated human mast cells. The method comprises contacting stimulated human mast cells with an agent which is an inhibitor of ATP binding to a P2-purinoceptor, preferably a P2Y-purinoceptor, most preferably the $P2Y_1$- or $P2Y_2$-purinoceptor; and assaying said cells for release of one or more mediators. The stimulated mast cells may comprise, for example, immunologically stimulated mast cells. Most preferably, the immunologically stimulated mast cells comprise lung mast cells. The preferred mediator for assay is histamine.

The invention is also a method for determining, in vitro, the effectiveness of an agent for the treatment of a human subject for a disorder characterized by undesirable release of mediator from stimulated mast cells. The method is a competitive binding assay in which the test agent competes with a P2-purinoceptor ligand for binding to a reagent comprising a P2-purinoceptor. The method comprises forming a mixture comprising the test agent, a P2-purinoceptor ligand (preferably a P2Y-purinoceptor ligand, most preferably a $P2Y_1$- or $P2Y_2$-purinoceptor ligand) and a reagent comprising a P2-purinoceptor (preferably a P2Y-purinoceptor, most preferably the $P2y_1$- or $P2Y_2$-purinoceptor); and assaying the mixture for the inhibition of ligand binding to the receptor by the agent. The ligand preferably comprises a receptor agonist. The reagent may comprise, for example, human mast cells, particularly lung mast cells. The assay is particularly useful for determining the effectiveness of agents for the treatment of disorders characterized by the undesirable release of histamine, such as allergy and asthma.

By "stimulated mast cell" is meant a mast cell in an activated state which is characterized by, or proximally leads to, degranulation and release of mediator from the cell. By "immunologically stimulated mast cell" is meant a mast cell which becomes stimulated by binding of antigen to IgE on the cell surface. Mast cell immunologic stimulation also includes experimental immunological stimulation achieved by contacting mast cells with antibodies to IgE, which results in the cross-linking of attached FcεR receptors on the mast cell.

By "P2-purinoceptor ligand" is meant a compound which binds to a P2-purinoceptor.

BRIEF DESCRIPTION OF THE FIGURES

FIG. 4 comprises a series of readouts from the high pressure liquid chromatography (HPLC) detection of purine compounds in cell culture media containing HLMC cells preincubated with $10^{-4}$ M ATP and subsequently incubated with or without anti-IgE (3 μg/ml).

DETAILED DESCRIPTION OF THE INVENTION

Figure 1:
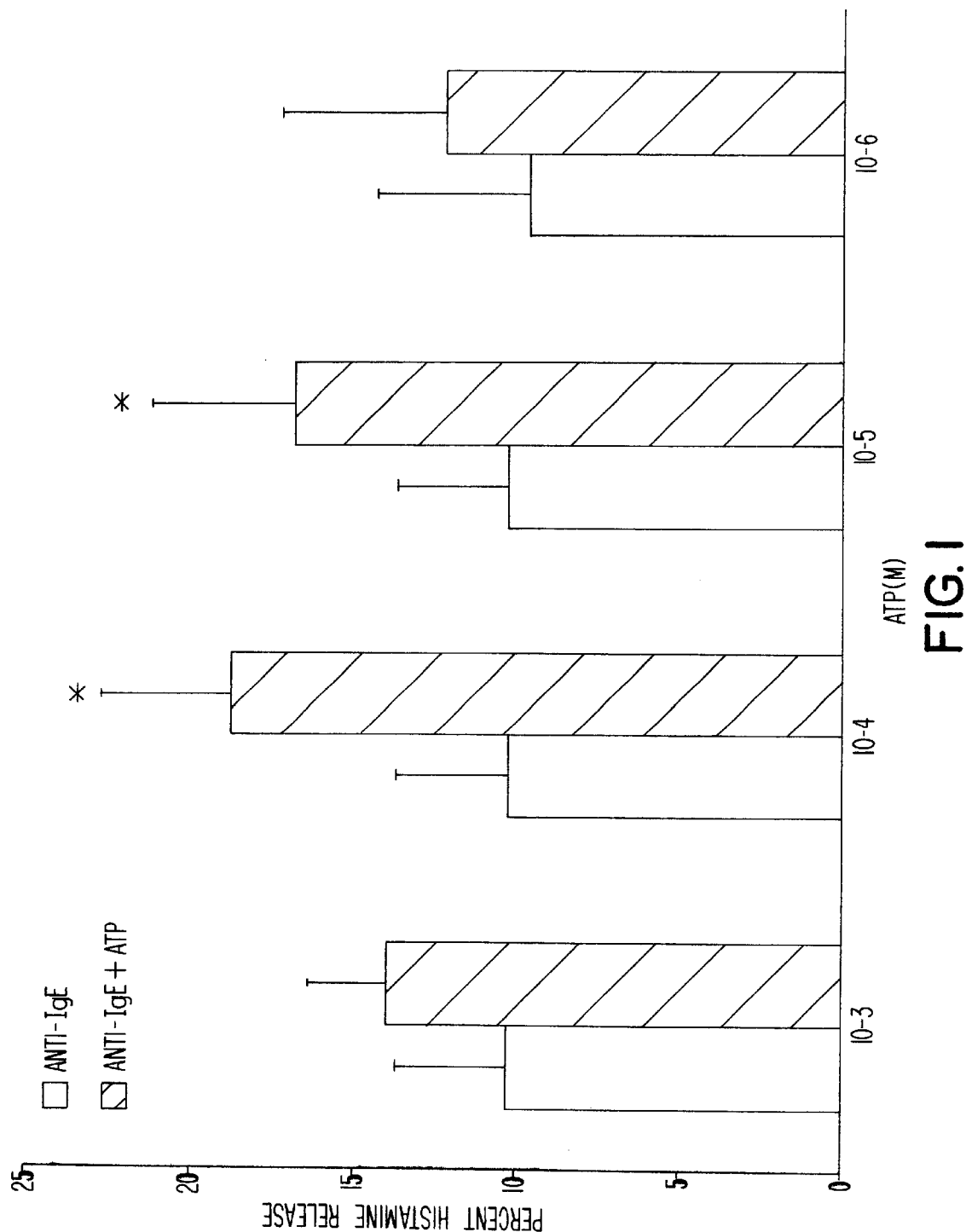
FIG. 1 is a graph of the dose-response relationship of the ATP-modulated histamine release from human lung mast cells (HLMC) induced by anti-IgE. ATP at various concentrations was added to cells 15 minutes prior to anti-IgE (3 μg/ml) challenge. Control cells received no ATP.

We have shown that ATP can modulate the release of mediators from stimulated human mast cells. ATP binding to stimulated human mast cells results in substantially enhanced mediator release. ATP binding to mast cells presents a target for therapeutic intervention in the treatment and management of disorders characterized by undesirable mediator release from mast cells.

As demonstrated herein, ATP enhancement of mediator release is not attributable to ectoenzymatic breakdown of ATP to adenosine. Also, adenosine, in contrast to ATP, is observed to exert a bimodal effect on anti-IgE-induced histamine release. At high adenosine concentration, histamine release is significantly inhibited; lower concentrations potentiated histamine release, though not significantly. Further, in absolute terms, the ATP enhancement effects were greater than those of equimolar doses of adenosine.

In addition to ATP, we have found that the pyrimidine nucleotide uracil triphosphate (UTP), as well as the following ATP analogs, are able to modulate mediator release from human mast cells: α,βmethylene-ATP (a,βmATP), β,γmethylene-ATP (β,γmATP) and 2methylthio-ATP (2mSATP). The structure-function cascade obtained by quantitative analysis of the relative effect of these compounds on histamine release is consistent with mediation of ATP-induced histamine release by a P2Y-purinoceptor on the mast cell surface. The finding of ATP modulation of mediator release from mast cells allows, for the first time, a mechanism for regulating that mediator release by perturbing ATP binding to its P2-purinoceptor on mast cells. Treatment of mast cell mediator-related disorders may be carried out by administration of molecules, most particularly analogs of ATP, which can competitively bind to P2-purinoceptors on the mast cell surface and block binding of the authentic receptor ligand ATP.

We have found that the action of ATP in mediating signal transduction in human mast cells is entirely different from the action of ATP on rat cells. ATP is able to induce histamine release from unstimulated rat peritoneal mast cells (Keller, *Tissue Mast Cells In Immune Reactions*, S. Karger, p. 38–39, 1966; Diamant, *Int. Arch. Allergy* 36:3–21, 1969; Sugiyama, *Japan. J. Pharmacol.* 21, 209–226, 1971; Cockcroft and Gomperts, *J. Physiol* 296, 229–243, 1979). Surprisingly, we have found that ATP alone, in the absence of any stimulatory signal, does not cause histamine release from HLMC. This is in stark contrast to the aforementioned studies wherein ATP alone caused, in a dose-dependent fashion, the direct triggering of histamine release in rat mast cells. Human mast cells which are not first stimulated by cross-linking of FcεRI surface receptors through antigen or anti-IgE binding, or other stimulatory signal, do not release mediators upon exposure to ATP. Moreover, it has been suggested that the receptor which mediates the action of ATP on rat mast cells is the ligand binding channel receptor $P2X_7$/P2Z, for which the agonist is the tetrabasic form of ATP, $ATP^{4-}$ (Tatham et al., *Euro. J. Pharmacol* 147, 13–21, 1988). This $ATP^{4-}$ receptor is distinct from the P2-purinoceptor which we have found responsible for ATP's action on HLMC. $ATP^{4-}$ forms complexes with $Ca^{2+}$ and $Mg^{2+}$. In our experiments reported herein, negligible amounts of $ATP^{4-}$ were present due to the inclusion of both $Ca^{2+}$ and $Mg^{2+}$ at millimolar concentrations in all assay buffers. Moreover, ATP challenge of HLMC in $Ca^{2+}$-free and $Mg^{2+}$-free media failed to provoke histamine release (results not shown).

There is yet further evidence of a different signal transduction mechanism for ATP's action on mediator release from rat versus human mast cells:

(1) ATP hydrolysis has been viewed as a requirement for rat peritoneal mast cell activation (Izushi & Tasaka, *Pharmacology* 42: 297, 1991). ATP hydrolysis is not required in order to modulate HLMC activation. Intact ATP is a modulator of HLMC activation (Example 6).

(2) Rat peritoneal mast cells display a bi-modal response to ATP. Maximum mediator secretion occurs with $ATP^{4-}$ at 2 μM, and is depressed by $Ca^{2+}$ and $Mg^{2+}$ (Cockfort & Gomperts, *Biochem J.* 188: 789, 1980). Stimulated HLMC, in contrast, display a dose-dependent mediator release response upon ATP binding in the presence of 1 mM each of $Ca^{2+}$ and $Mg^{2+}$ (Example 5).

(3) In the presence of millimolar $Ca^{2+}$, $ATP^{4-}$ at a concentration above 3 μM inhibits mediator release from rat peritoneal mast cells (Bennett et al., *J. Physiol.* 317: 334, 1981). ATP does not inhibit mediator release from human lung mast cells at any concentration (Example 2).

(4) The ATP analogs α,βmATP and β,γmATP are inactive in inducing mediator release in rat peritoneal mast cells (Id.). These same compounds are active in enhancing mediator release from HLMC (Example 3).

(5) The structure-function cascade of ATP-analog enhancement of mediator release differs in rat peritoneal and human mast cells. For rat peritoneal mast cells, the cascade is 2mSATP≧ATP>>α,βmATP=β,γmATP=0 (Tatham et al., *Eur. J. Pharmacol* 147:13, 1988). The structure-function cascade for HLMC is ATP>2mSATP≧α,βmATP≧β,γmATP (Example 3).

(6) Rat and human mast cells differ dramatically with respect to sensitivity to UTP. In comparison with ATP, UTP is almost inactive at $10^{-4}$M in achieving mediator release from rat peritoneal mast cells (Sugiyama, *Japan. J. Pharmacol.* 21:209, 1971). But we have found that UTP is very active in enhancing mediator release from stimulated HLMC (Example 4).

(7) Rat and human mast cells further differ in their response to magnesium ion. Whereas 1mM $Mg^{2+}$ inhibits ATP-induced histamine release from rat cells (Diamant, *Int. Arch. Allergy* 36:3, 1969), we have found that histamine release from HLMC is enhanced by ATP in the presence of 1mM $Mg^{2+}$ (Example 2).

(8) Preincubation of HLMC with the putative P2X-purinoceptor antagonist PPADS (Lambert et al., *Eur. J. Pharmacol.* 217:217–219, 1992) does not affect ATP modulation of anti-IgE-induced histamine release from the HLMC (Example 9), demonstrating that the ATP receptor on HLMC is a member of the P2Y family, not a member of the P2X family. The receptor which mediates the action of ATP on rat mast cells is a member of the P2X family.

According to the present invention, an inhibitor of ATP binding to P2-purinoceptors on human mast cells is utilized to treat human disorders which are characterized by the undesirable release of mediator from mast cells. By "inhibitor" is meant any agent that is capable of, directly or indirectly, interfering with ATP binding to a P2-purinoceptor which results in a reduction of ATP potentiation of mediator release from a mast cell. The inhibitor may take the form a P2-purinoceptor antagonist which forms a blockade against ATP binding to the P2-purinoceptor. Alternatively, the inhibitor may take the form of an allosteric modifier of the P2-purinoceptor. Such agents act by changing the conformation of the P2-purinoceptor to reduce receptor binding affinity for the ligand ATP.

The term "inhibitor" also includes agents which are partial agonists of ATP binding to P2-purinoceptors, and which are consequently competitive antagonists at the P2-purinoceptor. Those agents which are partial agonists of ATP modulation of human mast cell mediator release are considered inhibitory since their binding to the receptor competes with the authentic ligand, ATP, which has a greater level of activity upon binding to the P2-purinoceptor than the partial agonist.

Antagonists of P2-purinoceptors include, for example, suramin (Dunn and Blakely, *Br. J. Pharmacol.* 93:243–245, 1988); pyridzalphosphate-6-azophenyl-2',4'-disulfonic acid or PPADS (Lambrecht et al., *Eur. J. Pharmacol.* 217:217–219, 1992); adenosine-3'-phosphate-5'-phosphate or A3P5P; adenosine-3'-phosphate-5'-phosphosulfate or A3P5PS (Boyer et al., *Mol. Pharmacol.* 50:1323–1329, 1996); and the compound "Reactive Blue 2" which has the following structure:

Preferably, the P2-purinoceptor inhibitor is a specific P2Y-purinoceptor inhibitor, most preferably a $P2Y_1$- or $P2Y_2$-purinoceptor inhibitor. The human $P2Y_1$-purinoceptor has been cloned and reported by Schachter et al., *Br. J. Pharmacol.* 118:167–173, 1996, the entire disclosure of which is incorporated herein by reference. The human $P2Y_2$-purinoceptor has been cloned and reported by Parr et al., *Proc. Natl. Acad. Sci. USA* 91, 3275–3279 (1994) the entire disclosure of which is incorporated herein by reference.

Figure 5:
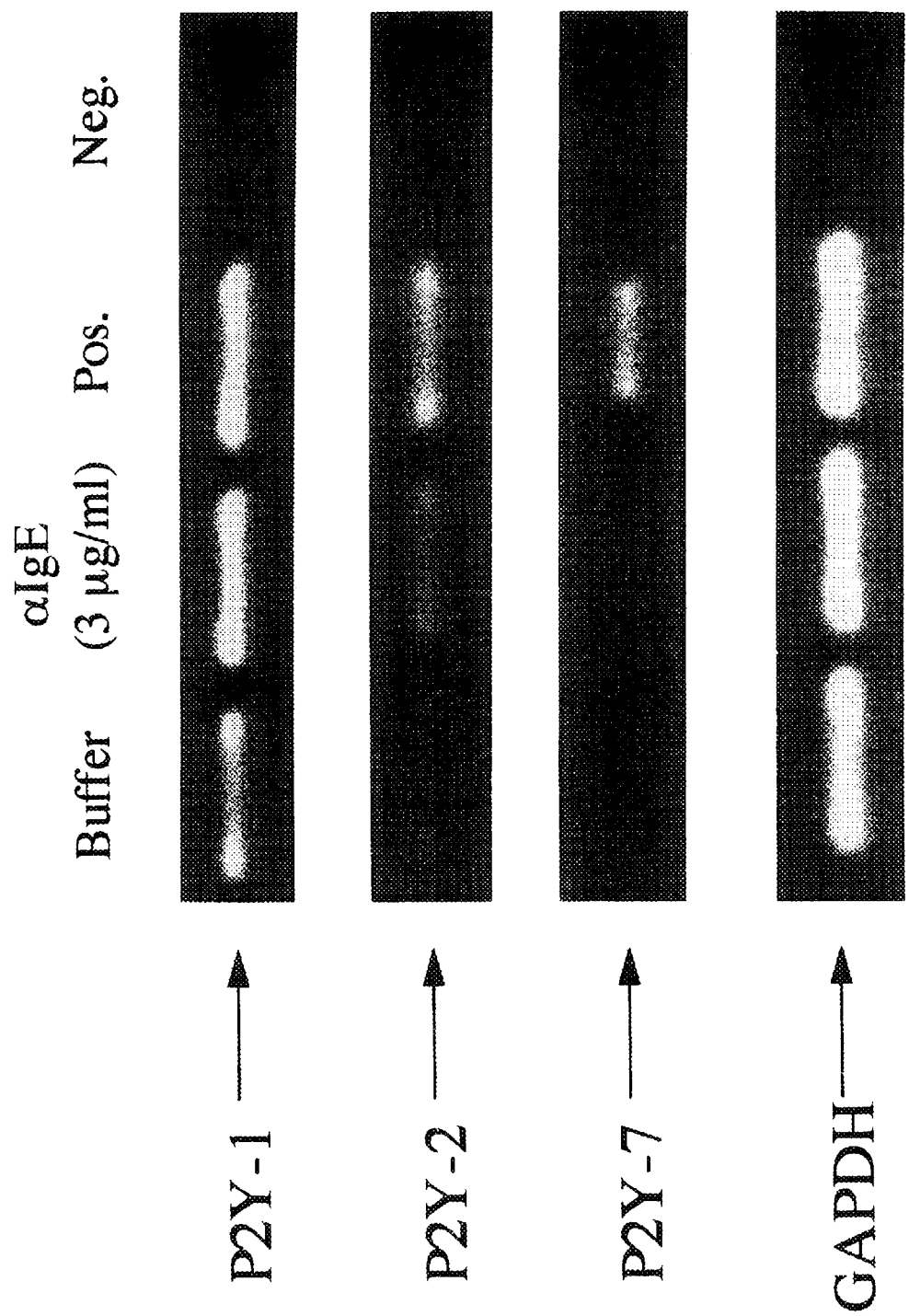
FIG. 5 is a blot of the reverse transcriptase-polymerase chain reaction (RT-PCR) amplification of $P2Y_1$-, $P2Y_2$- and $P2Y_7$-purinoceptor mRNA from HLMC challenged with either buffer of anti-IgE, followed by extraction of tcRNA.
Figure 6:
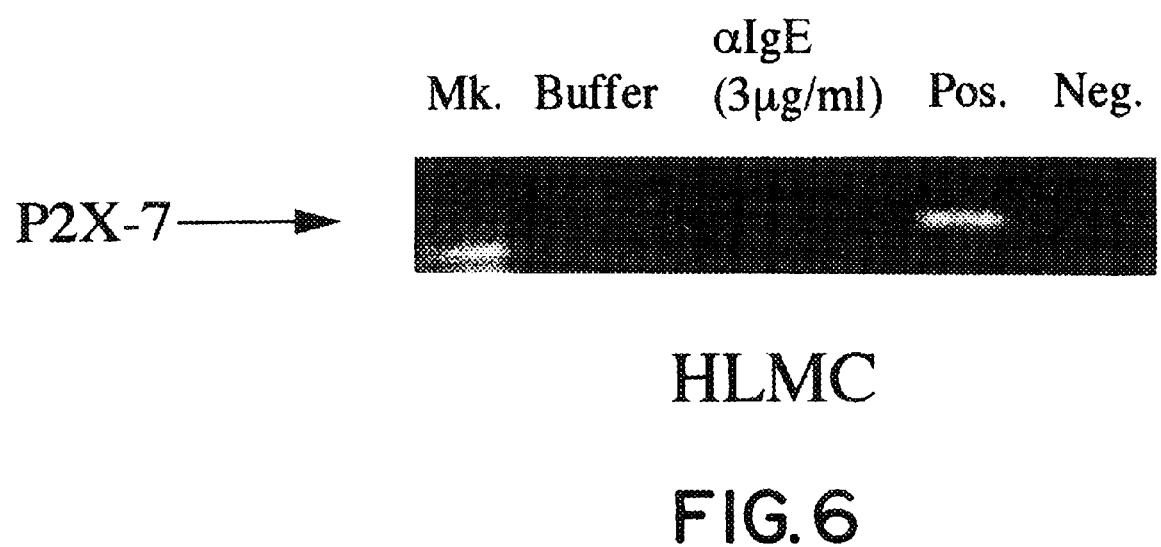
FIG. 6 is a blot of the RT-PCR amplification of $P2X_7$/P2Z-purinoceptor mRNA from HLMC challenged with either buffer or anti-IgE for two hours.

Without wishing to be bound by any theory, it is believed that the receptor on human mast cells which binds ATP and is thus responsible for ATP modulation of mediator release is the same as or similar in structure to the $P2Y_1$- or $P2Y_2$-purinoceptor. We have found that purified HLMC preparations constitutionally express the $P2Y_1$- and $P2Y_2$-purinoceptor (FIG. 5), but not the $P2X_7/P2Z$-purinoceptor (FIG. 6). The $P2X_7/P2Z$-purinoceptor is reported to mediate histamine release from rodent mast cells. We have also found that HLMC do not express the $P2Y_7$-purinoceptor (FIG. 5).

We have also observed that the structure-function cascade for ATP analog modulation of histamine release from human mast cells is indicative of the structure-function cascade a P2Y-purinoceptor, more particularly the $P2Y_1$-purinoceptor. With this in mind, the preferred P2-purinoceptor inhibitors for the practice of the present invention are adenosine-2'-phosphate-5'-phosphate or A2P5P, A3P5P, and A3P5PS. These compounds are specific competitive antagonists of the $P2Y_1$ subtype of purinoceptor and do not antagonize other P2-purinoceptors (Boyer et al., supra). A3P5P and A3P5PS in particular are preferred, as they are devoid of agonist activity at the human $P2Y_1$ receptor. Partial agonists of $P2Y_1$ include A2P5P and adenosine-2'-phosphate-5'-phosphoribose. Preferably, the P2-purinoceptor inhibitor used in the practice of the present invention is a specific inhibitor of ATP binding to the $P2Y_1$-purinoceptor, which does not bind substantially to other P2-purinoceptor types, including other P2Y subtypes.

An inhibitor of ATP binding to P2Y-purinoceptors on human mast cells is utilized to treat human disorders which are characterized by the undesirable release of mediator from mast cells. Such disorders include those conditions which give rise to mast cell stimulation and mediator release. Such conditions include, for example, asthma, allergy, bronchoconstriction and inflammatory lung disease. Mast cells undergo immunological stimulation by binding of antigen to cell surface IgE. Mast cells, particularly lung mast cells, may also undergo stimulation by nonimmunologic means. For example, mast cells may be stimulated to release mediator by signals such as contact with cold air, ingestion of aspirin or aspirin-like drugs, and vigorous exercise.

Pulmonary embolism is associated with massive activation of platelets. Activated platelets release large amounts of ATP. The ATP released from activated platelets during acute pulmonary embolism can exacerbate histamine (and other mediators) release from mast cells and other inflammatory cells. Exacerbation of histamine release from lung mast cells results in bronchoconstriction. Inhibition of ATP binding to P2-purinoceptors on mast cells is thus particularly useful in the treatment of bronchoconstriction associated with the acute phase (onset) of pulmonary embolism.

While the principle usefulness of the invention resides in inhibiting ATP binding to lung mast cells to counteract bronchoconstriction arising from stimulation of the mast cells and the resulting mediator release, the utility is not limited to modulation of lung mast cell response. Mast cells also populate the skin, nose, eye, gut and skeletal joints. Mast cells of the gut and joints share similar morphology with lung mast cells, and are therefore likely to yield to modulation of mediator release by inhibitors of ATP binding in the same fashion as lung mast cells.

In accordance with the present invention, a compound which inhibits ATP binding to a P2-purinoceptor may be administered in therapeutically effective amounts in accordance with methods appreciated by those skilled in the art. The inhibitor compound is preferably a P2Y-purinoceptor antagonist, more preferably a $P2Y_1$- or $P2Y_2$-purinoceptor antagonist. The mode of administration includes any means that produces contact of the active ingredient with the site of action in the body of a human being, such as in a human body fluid or tissue. These modes of administration include but are not limited to oral, topical, hypodermal, intravenous, intramuscular, inhalational and parenteral methods of administration. In one preferred embodiment of the invention, the target tissue comprises lung mast cells, and the method of administration comprises inhalation into or injection into the lung. The P2-purinoceptor antagonist may be administered singly or in combination with other P2-purinoceptor antagonists, or with other active agents. The antagonists are preferably administered with a pharmaceutically acceptable carrier selected on the basis of the selected route of administration and standard pharmaceutical practice.

Methods of administering pharmaceuticals to the lung by inhalation are well-known to those skilled in the art. The design of suitable inhaler devices is described, for example in *Remington's Pharmaceutical Sciences,* 17th ed., Mack Publishing Co., Easton, Pa., 1985, p. 181–182, incorporated herein by reference.

The dosage of P2-purinoceptor antagonist administered in the practice of the therapeutic method of the invention in any particular instance will depend upon factors such as the pharmacodynamic characteristics of the particular antagonist; its mode and route of administration; the age, health, and weight of the recipient; the nature and extent of symptoms; the types of concurrent treatment; the frequency of treatment; and the effect desired. It is contemplated that a daily dosage of a P2-purinoceptor antagonist according to the practice of the present invention is in the range of from about 1 $\mu$g to about 100 mg per kg of body weight, preferably from about 10 $\mu$g to about 20 mg per kg of body weight, per day. Pharmaceutical compositions may be administered in a single dosage, divided dosages or in sustained release. Persons of ordinary skill will be able to determine dosage forms and amounts with only routine experimentation based upon the present disclosure.

The method of therapeutic administration of P2-purinoceptor antagonist includes administration as a pharmaceutical composition parenterally in sterile liquid dosage forms or topically in a carrier. The antagonist may be formulated into dosage forms according to standard practices in the field of pharmaceutical preparations. See Gennaro Alphonso, ed., *Remington's Pharmaceutical Sciences,* 18th Ed., (1990) Mack Publishing Co., Easton, Pa.

For parenteral administration, the P2-purinoceptor antagonist may be mixed with a suitable carrier or diluent such as water, an oil, saline solution, aqueous dextrose (glucose) and related sugar solutions, or a glycol such as propylene glycol or polyethylene glycol. Solutions for parenteral administration preferably contain a water soluble salt of the P2-purinoceptor antagonist. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propylparaben, and chlorbutanol.

According to another aspect of the invention, potential therapeutic compounds for the treatment of asthma and other disorders characterized by undesirable mediator release from mast cells, are identified by a mast cell assay which relies on mediator release. Test cells comprising stimulated human mast cells are contacted with a candidate agent which is an inhibitor of ATP binding to a P2-purinoceptor. The agent is preferably a compound which is a small molecule suitable for human therapeutic use. The test cells are then assayed for the release of one or more mediators. The assay is advantageously carried out as an in vitro assay.

The test cells advantageously comprise fresh HLMC. Fresh HLMC may be obtained by a three-day purification protocol which commences with formation of a single cell suspension by enzymatically dispersing freshly harvested lung tissue, followed by filtration and density fractionation to obtain an HLMC cell population of greater than 85% purity. The purified HLMC are incubated with the candidate compound, after which ATP is added. The cells are stimulated by addition of an effective amount of anti-IgE antibody, which simulates cross-linking of Fc$\epsilon$RI receptors by antigen. Cells in a control group are immunologically stimulated with prior addition of the candidate compound in one subgroup, and without ATP in another subgroup. The extent of mediator release is determined in all cell groups. The difference between the extent of mediator release by cells treated with ATP and the candidate compound on the one hand, and cells treated with ATP on the other hand, is a measure of the compound's effectiveness in reducing ATP modulation of mast cells, and the compound's potential usefulness as a therapeutic agent for inhibiting undesirable mediator release.

Preferably, the released mediator which is subject to assay is histamine. Cell culture supernatant histamine may be measured by an automated procedure in which histamine is condensed with orthophthaldialdehyde and fluorescence.

According to another aspect of the invention, a screening test for potential therapeutic agents is provided which relies on assaying of an agent's ability to compete with a P2-purinoceptor ligand for binding to a P2-purinoceptor. The ligand may comprise any compound which is capable of mimicking ATP binding to a P2-purinoceptor. The P2-purinoceptor and ligand are preferably a P2Y-purinoceptor and P2Y-purinoceptor ligand, respectively, more preferably a $P2Y_1$- or $P2Y_2$-purinoceptor and $P2Y_1$- and $P2Y_2$-purinoceptor ligand, respectively.

According to a preferred embodiment, a test compound competes with a $P2Y_1$-purinoceptor ligand for binding to a reagent comprising a $P2Y_1$-purinoceptor. A mixture is formed comprising the test compound, a $P2y_1$-purinoceptor ligand, and a reagent comprising the $P2Y_1$-purinoceptor. The mixture is then assayed for the ability of the test compound to inhibit the ligand's binding to the receptor. Inhibition of ligand binding is suggestive of a compound's ability to inhibit mast cell mediator release, and its usefulness as a potential therapeutic. A compound proven effective in the ligand binding screen may then be tested further to establish whether the competitive inhibition results in $P2Y_1$-purinoceptor antagonism.

The reagent comprising a P2-purinoceptor in the ligand binding inhibition assay may be whole cells, cell membranes or fragments of cell membranes containing the receptor. Preferably, the reagent comprises fresh HLMC or HLMC membranes. The reagent may also comprise a cell line expressing a P2-purinoceptor, such as the cell line HMC-1, derived from a mast cell leukemia patient (Butterfield et al, *Leuk. Res.* 4:345, 1988). The HMC-1 cell line expresses the $P2Y_1$-purinoceptor.

The P2-purinoceptor ligand in the ligand binding inhibition assay advantageously comprises a radioactively labeled compound ("radioligand"), and the assay may take the form of a radioligand binding assay. Radioligand binding assay procedure for biological receptors, and radioligand binding assays for the $P2Y_1$-purinoceptor in particular, are known in the art. See for example, Simon et al, *Eur. J. Pharmacol.*, 291, 281–289 (1995) ($P2y_1$-purinoceptor); Tsukagoshi et al., *J. Pharmacol. Exp. Ther.* 273, 1257–1263 (1995) (bradykinin receptor); Belardinelli et al., *Circ. Res.*, 79(6), 1153–1160 (1996) ($A_{2A}$ adenosine receptor). The entire disclosures of Simon et al., Tsukagoshi et al. and Belardinelli et al. are incorporated herein by reference. For testing a candidate agent's ability to inhibit ligand binding to the $P2Y_1$-purinoceptor, the radioligand may advantageously comprise, for example, $[^{35}S]3'$-deoxyadenosine $5'$-O-(1-thio)triphosphate ($[^{35}S]dATP\alpha S$) or $[^3H]$uridine $5'$-triphosphate ($[^3H]UTP$) (Simon et al., supra). Aliquots (0.5 ml final volume) of freeze-thawed HLMC membrane fraction containing from 5–100 µg, preferably 5–10 µg, protein are incubated with drug at a concentration in the range of $10^{-11}$–$10^{-4}$M and a concentration of radioligand which is sufficient to saturate the available $P2Y_1$-purinoceptors. The effect of the drug on the radioligand binding to the receptor (specific binding) is determined. Assays are also conducted to identify total and nonspecific binding of the radioligand to the sample. For the specific assay results to have validity, nonspecific binding of radioligand should not exceed about 30% of radioligand total binding to the samples.

The practice of the invention is illustrated by the following nonlimiting examples.

EXAMPLE 1

Purification of Human Lung Mast Cells

Day 1. Enzymatic Dispersion of Human Lung Tissue. Grossly normal human lung tissue obtained within minutes of resection is dissected free of tumor, then finely minced and thoroughly washed in divalent cation free Tyrode's buffer. Minced fragments are enzymatically dispersed into a single cell suspension by two 30 minute incubations at 22 degrees in the enzymes Pronase (2 mg/ml) and chymopapain (0.5 mg/ml), followed by two similar incubations in collagenase (1 mg/ml) and elastase Type I (10 units/ml). Liberated cells are harvested through Nytex nylon (100 micron pore size) after each digestion and thoroughly washed in Tyrode's buffer to which gelatin (1 g/L), magnesium (1 mM) and deoxyribonuclease (15 mg/ml) (TGMD) have been added. Cells (20–100×$10^6$, mast cells of 5.6±1.8% purity) are resuspended in culture media consisting of RPMI 1640, L-glutamine (1 mM) and gentamicin (100 µg/ml), and incubated overnight in 100 mm tissue culture plates at 25° C.

Day 2. Elutriation and Dose-response curve. The following morning, non-adherent cells are washed from the plates, then sedimented at 150×g for 8 minutes. Adherence of cell contaminants and attrition of contaminating cells in culture increases mast cell purities to 11.4±2.1%. Mast cell recovery is usually complete. Suspensions containing 20–100×$10^6$ mast cells are subject to counter-current centrifugation elutriation (CCE) as follows. The cells are loaded into an elutriation chamber housed in a Beckman JE21 rotor housed in a J6B centrifuge. At a constant rotor speed (1820±5 rpm), buffer (TGMD) flow entering the bottom of the elutriation chamber and flowing in the direction counter to centrifugal force is increased in pre-defined increments. Cells are loaded at a buffer flow of 11 ml/minute, then flow increased to 12, 14, 18, 20, 26 and 30 ml/minute. At each change of flow, 150 ml fractions are collected. The incremental increases in buffer flow carries cells of ever-increasing diameter out of the chamber. The majority of HLMC, because of their large diameters in comparison to other lung cells, selectively elute in the later fractions in purities ranging from 20–85%. Cells in each fraction are sedimented, then counted by the Alcian blue technique to determine total cell and mast cell numbers. Fractions most enriched for mast cells are cultured overnight at 37° C., to allow more adherence of contaminating macrophages and then further purified over Percoll density gradient fractionations. When time permits on Day 2, a preliminary dose-response curve to anti-IgE is performed to access the capacity of cells to respond.

Day 3. Percoll Density Fractionation and Purification. Density gradient fractionation can be performed after CCE on day 2, but the most pure mast cell preparations result on Day 3 after overnight culture. HLMC purification is performed by flotation through discontinuous Percoll gradients. Approximately 1–2×$10^7$ cells are suspended in 1.0 ml of "100%" Percoll (9 parts Percoll plus 1 part of 10×Hanks' balanced salt solution, HBSS) and layered at the bottom of a 12×75 mm polystyrene culture tube. Over the cell suspension are layered 0.8 ml aliquots of 80%, 70%, 60%, 50% and 40% Percoll solutions, prepared from a stock of 100% Percoll. The gradient is then centrifuged at 400×g for 10 minutes; cells at each interface are collected, washed twice in TGMD and counted. Purified HLMC (>85–99% pure) usually float to 60/70%, and/or 70/80% interfaces depending on the properties of mast cells from individual lungs.

EXAMPLE 2

Alternative Method for Purification of Human Lung Mast Cells; Effect of ATP on Histamine Release from Human Lung Mast Cells A. Buffers Lung fragments were washed with Tyrode's buffer containing (g/l): NaCl, 8.0; KCl, 0.2; $NaH_2PO_4$, 0.05; and glucose, 1.0. The buffer was titrated to pH 7.2 by the addition of $NaHCO_3$. Mast cell isolation and elutriation were performed in a buffer designated "TGMD", prepared from Tyrode's buffer to which the following were added (g/l): gelatin (1.0), magnesium (0.25; 1 mM), and DNase (0.01). The buffer designated "PAGCM" was a Pipes-albumin (0.003%) buffer containing (g/l): glucose (1.0), $CaCl_2.2H_2O$, 0.14 (1 mM); and $MgCl_2.6H_2O$, 0.2 (1 mM).

B. Human Lung Mast Cells

Mast cells were dispersed from human lung by methods previously reported (Schulman et al., *J. Immunol.* 29:2662–2667 (1982); Schulman et al., *J. Immunol.* 131:1936–1941 (1983)). Briefly, lung specimens obtained at thoracotomy for bronchogenic carcinoma were finely minced and extensively washed in divalent cation-free Tyrode's buffer. Fragments were briefly incubated in a mixture of pronase (2 mg/ml) and chymopapain (0.5 mg/ml). Freed cells were harvested through Nytex nylon cloth (150 microns pore size). Residual fragments were further exposed to a mixture of collagenase (1 mg/ml) and elastase (10 units/ml). All incubations and washes were performed at 37° C.; recovered cells were immediately washed three times in large volumes of TGMD. Mast cell purities in these human lung cell suspensions ranged from 1–8% as determined by alcian blue staining (Gilbert et al., *Blood* 46:279–285 (1975)). Lung mast cells were further purified, by counter-current elutriation, using previously reported methods (Schulman et al., *J. Immunol.* 131:1936–1941 (1983)). Mast cells were purified (80–>98%) by flotation of enriched elutriation fractions through a discontinuous Percoll gradient (Ishizaka et al., *J. Immunol.* 130:2357–2362 (1983)). Further mast cell purification was accomplished by immunomagnetic negative selection against CD2, CD3, CD4, CD8, CD14, CD16, CD21 and HLADR to ensure against contamination by T cells, B calls, NK cells, monocytes, and dendritic cells prior to mast cell stimulation using previously described methods (Jaffe et al., *Am. J. Respir. Cell. Mol. Biol.* 13:665–675 (1995); Jaffe et al., *Am. J. Respir. Cell. Mol. Biol.* 15:473–481 (1996)).

C. Histamine Release Assay

Mast cells ($10$–$50 \times 10^3$/tube) were preincubated in either buffer alone or buffer solutions, each containing ATP for 15 minutes, then challenged with buffer or anti-IgE at 37° C. in PAGCM. The concentrations of anti-IgE produce 30–70% of maximal release. Twenty minutes following activation, cells were rapidly pelleted and supernatants removed for histamine analysis. Histamine release was expressed as the net histamine released divided by the total histamine content× 100%. The total cellular histamine content was determined following cell lysis with 2% perchloric acid. Spontaneous histamine release was always <2% of cellular histamine and generally <1%. Histamine measurements were performed using the automated spectrofluorometric method of Technicon (Tarrytown, N.Y.). Variations between replicates were consistently <5%. All assays were run in duplicates.

D. Results

Incubation of purified HLMC with ATP at concentrations ranging from $10^{-7}M$–$10^{-3}M$ did not directly induce histamine release (n=23). In 20/23 preparations in which HLMC responded to anti-IgE stimulation, ATP at $10^{-4}M$ enhanced histamine release in all (10.9+2.7% histamine release to 19.2+2.9% histamine release, p<0.01). In 9 of these 20 anti-IgE-responsive preparations (control anti-IgE-induced release of 10.1+3.4%, n=9) the dose-dependent effects of ATP were examined from $10^{-5}M$ to $10^{-3}M$ (FIG. 1). In six of the nine, ATP at $10^{-6}M$ was examined. In these six preparations, ATP ($10^{-6}M$) had no effects on anti-IgE-induced histamine release. In 9 of 9 experiments, ATP at both $10^{-5}M$ and $10^{-4}M$ enhanced histamine release (p<0.05). ATP at $10^{-3}M$ enhanced anti-IgE-induced release in 7/9 experiments and in 2/9, inhibited release. Overall, this enhancement by ATP ($10^{-3}M$) to 14.0+2.4%, was not statistically significant (p>0.05). In 3/23 preparations that failed to respond to anti-IgE alone, preincubation with ATP ($10^{-6}$–$10^{-3}M$) was without effect.

Figure 2:
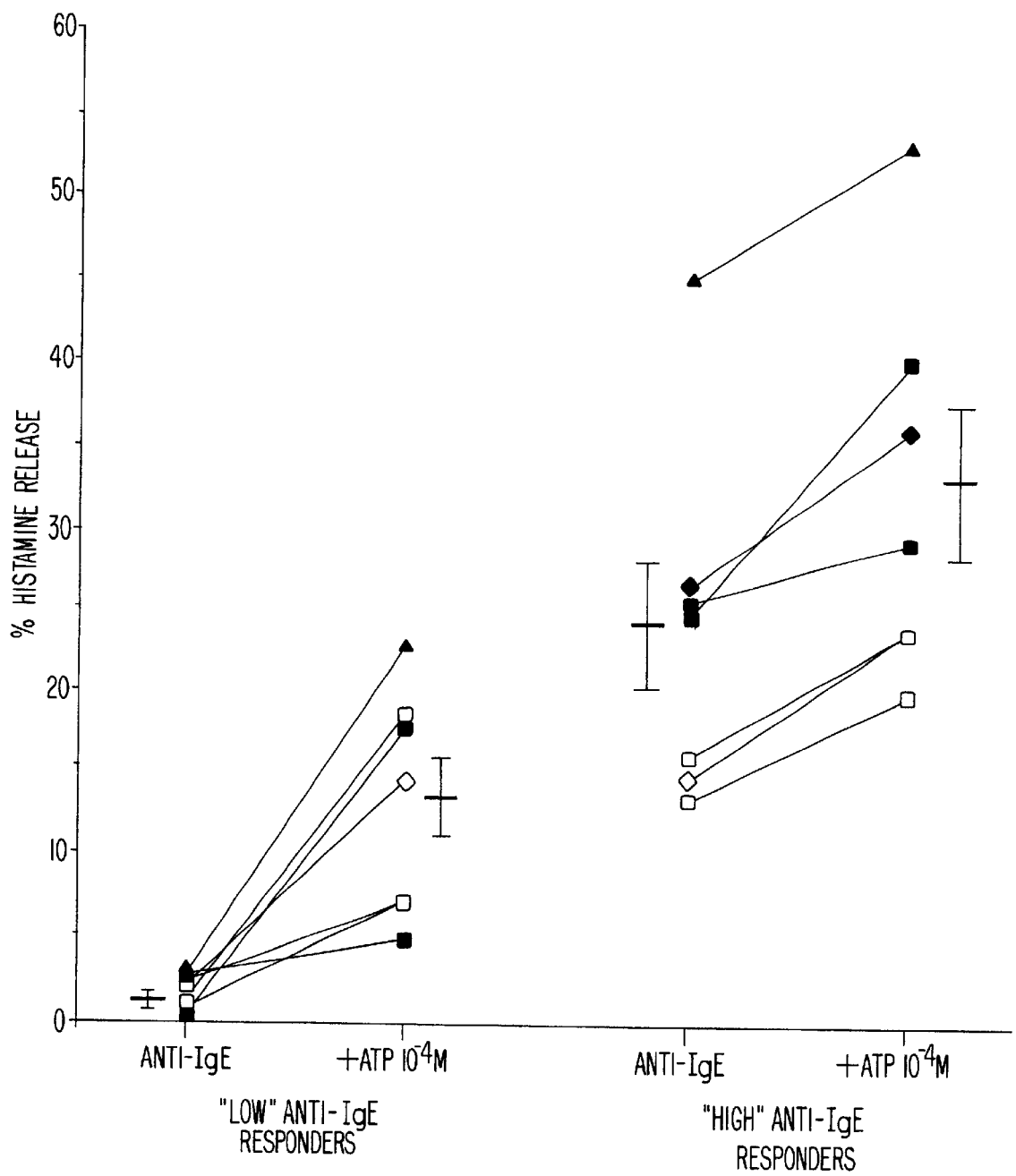
FIG. 2 is a graph of the potentiation by ATP ($10^{-4}$ M) of anti-IgE-induced histamine release from HLMC. The results are grouped into preparations in which anti-IgE induced release of histamine was less than 3% ("low responders") versus preparations in which anti-IgE induced release of histamine was equal to or greater than 14% ("high responders"). Shown are results obtained in 13 out of a total of 20 preparations representing extremes of response to ATP.

The relationship between the lowest and highest anti-IgE responsive preparations to the effects of ATP ($10^{-4}M$) were contrasted (FIG. 2). Interestingly, ATP enhanced anti-IgE-induced histamine release by ~8–10% at both extremes. Therefore, in terms of percent enhancement, the ATP effects were most striking when anti-IgE-induced release was low. Specifically, in experiments with a low (<3%) net anti-IgE-induced release (1.8±0.4%, range 0.5–2.9%, n=6), ATP ($10^{-4}M$) enhanced release to 13.5±2.7%, (750% enhancement). Anti-IgE-induced histamine release of 24.2±4.2% (range 14.0–45.9%, n=7) was enhanced by ATP ($10^{-4}M$) to 32.9±4.5%, representing only a 35% enhancement.

EXAMPLE 3

Effect of ATP Analogs on Histamine Release from Human Lung Mast Cells

The procedure of Example 2 was repeated, substituting the following for ATP: α,βmethylene-ATP (a,βmATP), β,γmethylene-ATP (β,γmATP) and 2methylthio-ATP (2mSATP). In ten experiments, the effect of these ATP analogues on anti-IgE-induced histamine release were determined. Anti-IgE-induced release of 9.9±3.1% was enhanced by all compounds. In 8/10 experiments, ATP itself was the most potent enhancer (17.7±4.1%). In 2/10, 2-mSATP was the most potent, and in 5/10, was the second most potent analogue (14.3±3.9%, n=10). The enhancement by the purine nucleotides of histamine release was inversely related to the efficacy of anti-IgE alone in releasing histamine. The structure-function cascade for the action of the purine nucleotides, was ATP≧2mSATP>α,βmATP>β,γmATP, indicating mediation by a P2Y-purinoceptor (Abbracchio et al., *Pharmacol. Ther.* 64:445–475 (1994)).

EXAMPLE 4

Effect of UTP on Histamine Release from Human Lung Mast Cells

Because P2Y2 purinoceptors have been shown to be widely expressed in immune cells, ATP was compared to uracil triphosphate (UTP), the preferred agonist for this receptor, for effects on anti-IgE-induced histamine release. The procedure of Example 2 was repeated, substituting UTP for ATP. In this group of six experiments, control anti-IgE-induced histamine release of 14.9±3.9% was enhanced by ATP ($10^{-4}M$) to 23.0±4.7 (p<0.05) compared to 19.2±5.0% (p<0.05) in the presence of equimolar UTP. Thus, UTP was less potent than ATP in modulating anti-IgE-induced histamine release.

EXAMPLE 5

Effect of Adenosine on Histamine Release from Human Lung Mast Cells

Figure 3:
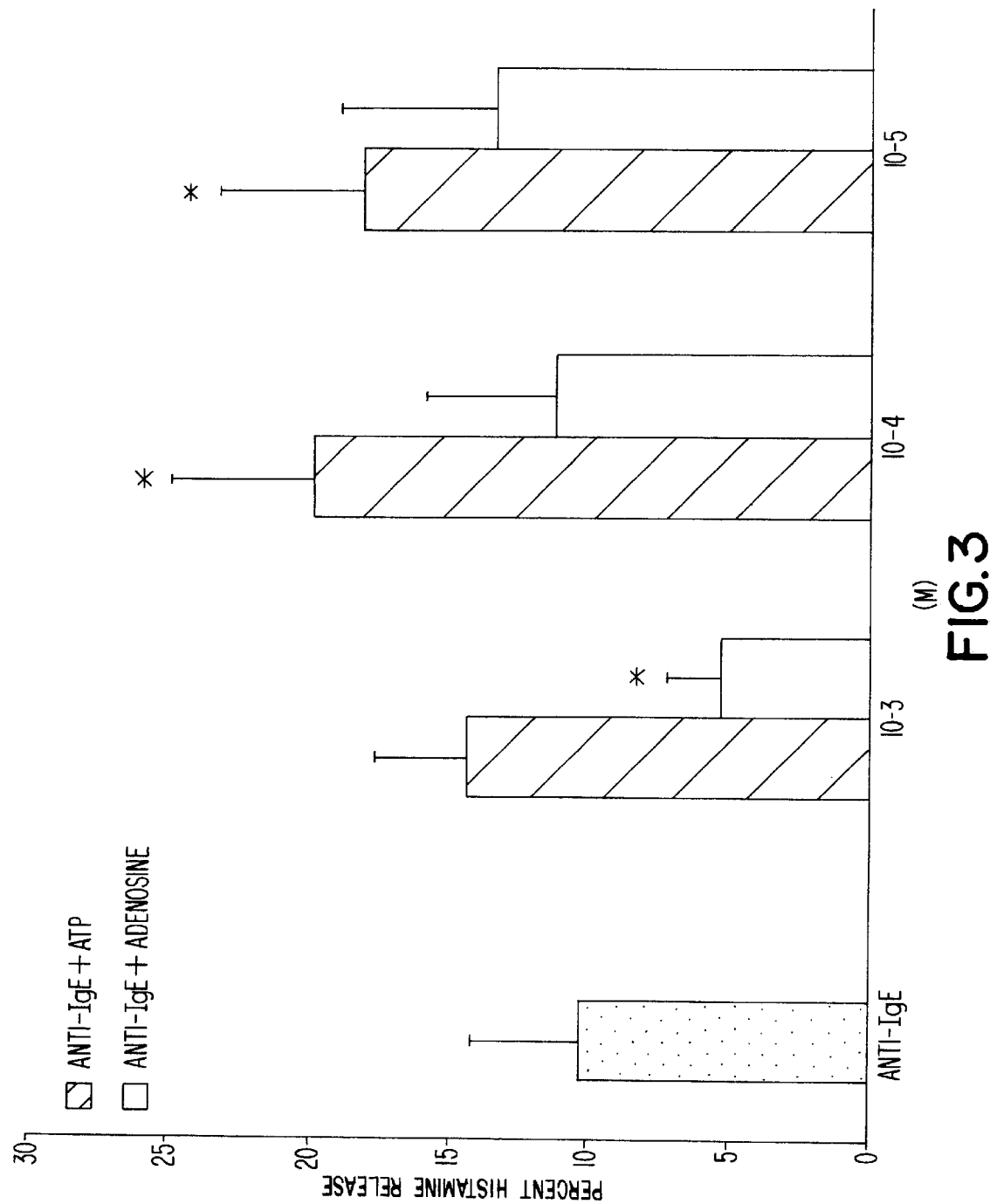
FIG. 3 is a graph of the comparative modulatory effects of ATP and adenosine on anti-IgE-induced histamine release from HLMC.

Since ATP is degraded to adenosine by ectoenzymes (Olsson et al., *Physiol. Rev.* 70:761–845 (1990)) and adenosine modulates histamine release from rat and human mast cells and basophils (Ott et al., *Int. Arch. Allergy. Immunol.* 98:50–56 (1982); Church et al., *Br. J. Pharmacol.* 80:719–726 (1983); Hughes et al., *Biochem. Pharmacol.* 33:3847–3852 (1984); Church et al., *Br. J. Pharmacol.* 87:233–242 (1986); Peachell et al., *Am Rev. Respir. Dis.* 138:1143–1151 (1988); Lohse et al., *Br. J. Pharmacol.* 98:1392–1398 (1989); Post et al., *Agents Actions* 30:30–33 (1990); Peachell et al., *J. Pharmacol. Exp. Ther.* 256:717–726 (1991); Feoktistov et al., *J. Clin. Invest.* 96:1979–1986 (1995); Ali et al., *J. Pharmacol. Exp. Ther.* 276:837–845 (1996); Fozard et al., *Eur. J. Pharmacol.* 298:293–297 (1996)), the effect of adenosine on histamine release from HLMC was also determined. The procedure of Example 2 was repeated, substituting adenosine for ATP. In six does-response experiments (FIG. 3), previous observations (Peters et al., *Am. Rev. Respir. Dis.* 126:1034–1039 (1982) were confirmed: adenosine alone did not directly induce histamine release from HLMC, but exerted a bimodal modulatory effect on anti-IgE-induced histamine release: anti-IgE-induced release of 10.3±3.0% was inhibited by adenosine at $10^{-3}$ M to 5.3±1.9% (p<0.05). At lower concentrations ($10^{-4}M$–$10^{-5}M$), adenosine enhanced histamine release to 11.2±4.7% and 13.4±5.6%, respectively, but neither effect was statistically significant (n=6). In these same experiments, ATP at both $10^{-4}$M and $10^{-5}$M significantly enhanced anti-IgE-induced histamine release.

EXAMPLE 6

Functional EctoATPase Assay of Human Lung Mast Cells

Figure 4A:
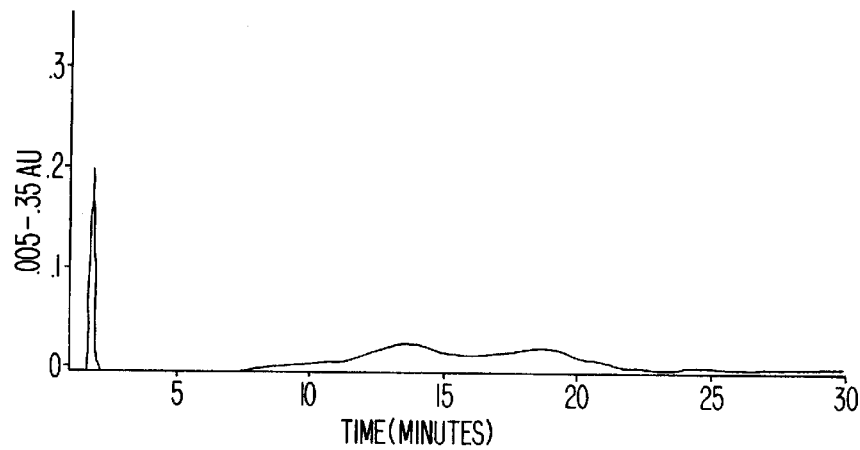
FIG. 4A: anti-IgE-activated HLMC.
Figure 4B:
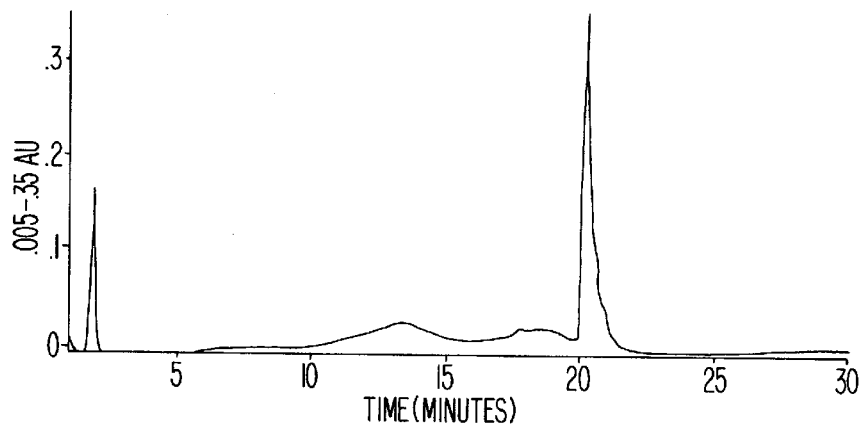
FIG. 4B: anti-IgE-activated HLMC+$10^{-4}$ M ATP.
Figure 4C:
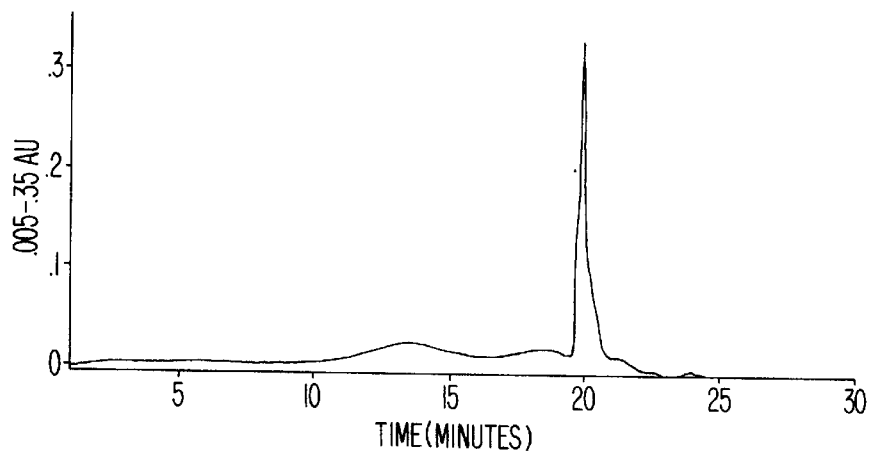
FIG. 4C, $10^{-4}$ M ATP alone without HLMC (control). The data are the result of three experiments. The arrow indicates the peak for ATP.

To determine whether the effects of extracellular ATP on purified HLMC may be mediated in part by degradation to adenosine, the potential ectoenzymatic breakdown of ATP to adenosine was examined by HPLC. Accordingly, HLMC (0.3–1.0×$10^5$) in 250 μl PAGCM (n=3) were preincubated with $10^{-4}$M ATP for 15 minutes and subsequently incubated with or without anti-IgE (3 μg/ml) for an additional 20 minutes. Control preparations were HLMC without ATP as well as a solution of $10^{-4}$M ATP in PAGCM. The supernatants were separated from the cells by centrifugation at 14,000-×g for 5 minutes and kept at −20° C. until analyzed by HPLC. The method of Stocci et al., Anal. Biochem. 167:181–90 (1987) was used for the detection of the purine compounds. The HPLC system consisted of Waters 600E controller, Waters Novapak 4 μm 3.9×150 mm $C_{18}$ column, and a 990 photodiode array detector. The solvent consisted of 0.1 mM $KH_2PO_4$, 8 mM tetrabutylammonium hydrogen sulfate (TAHS) pH 6.0 (buffer A), and 0.1 mM $KH_2PO_4$, 8 mM TAHS pH 6.0 with 30% (v/v) methanol (buffer B). The flow rate was 1 ml/min. with the following gradient program: 100% A to 2.5 min., linear gradient to 20% B at 5 min, to 40% B at 10 min., to 100% at 13 min., then 100% B to 30 min. 100 μl of supernatant (neat) was injected and the separation monitored at 254 nm over the 30 minute run time. The ATP peak areas were calculated and compared among the conditions. The data are shown in FIGS. 4A–C: 4A, anti-IgE-activated HLMC; 4B, anti-IgE-activated HLMC+ $10^{-4}$M ATP; 4C, $10^{-4}$M ATP alone without HLMC (control). The data are the result of three experiments.

There was no noticeable decrease in the area under the ATP peak (arrows at 20 min. in FIG. 4) for anti-IgE activated HLMC in the presence of $10^{-4}$M ATP (FIG. 4B) versus the control ($10^{-4}$M ATP alone without HLMC) (FIG. 4C). No additional peaks corresponding to ATP metabolites (i.e., ADP, AMP, adenosine were generated by the anti-IgE-activated HLMC (FIG. 4B). The early peak in FIG. 4 is the solvent front artifact and the low broad peaks are due to the change in solvent composition.

HLMC thus failed to demonstrate functional ectoATPase activity. Human lung fragments under identical conditions demonstrated conversion of ATP to adenosine over the 15 minute incubation period (data not shown).

EXAMPLE 7

Effect of ATP Receptor Antagonist on Histamine Release from Human Lung Mast Cells To confirm the effect of a putative P2-purinoceptor antagonist as an inhibitor of mast cell histamine release, the procedure of Example 2 is followed, with the following modification. HLMC are incubated for 15 minutes with the putative antagonist alone added to the assay at time t=−30 minutes, prior to the addition of buffer or ATP at time t=−15 minutes. The effect of the putative antagonist on mast cell activation is determined by comparing the level of histamine release from the anti-IgE-challenged HLMC with and without preincubation of the cells with receptor antagonist.

EXAMPLE 8

Inhibition of Ligand Binding to P2Y-Purinoceptor

The ability of a candidate pharmacological agent to inhibit ligand binding to the $P2Y_1$-purinoceptor on human lung mast cells is determined as follows. The procedure may be used as a preliminary screen in identification of possible $P2Y_1$-purinoceptor antagonists.

A. Preparation of Human Lung Mast Cells Membranes. Fresh human lung mast cells are obtained as in Example 1. A crude membrane fraction is then generated according to the procedure of Simon et al., Eur. J. Pharmacol. 291, 281–289 (1995), the entire disclosure of which is incorporated herein by reference. Essentially, the harvested HLMC are suspended in a buffer A. Buffer A has the composition: 50 mM Tris/1 mM EDTA/1 mM EGTA, adjusted to pH 7.4 with HCl, and also contains (as protease inhibitors) 1 mM benzamidine, 0.1 mM phenylmethylsulphonyl fluoride, 0.01% bacitracin, 0.001% soybean trypsin inhibitor and 40 kallikrein inhibition units of aprotinin. The suspended cells are freeze-thawed and further disrupted by homogenization with a Ultra-Turrax J-25 homogenizer (2×15 s, setting 5, cooling the suspension for 1 minute between pulses). The membranes are collected by centrifugation at 12000×g, 30 minutes in a microcentrifuge at 4° C. The supernatant is discarded, the membranes are resuspended in buffer A (1 ml) by passing through a 21-gauge sterile needle and incubated on ice (30 minutes) to chelate endogenous divalent cations, destroy labile endogenous ligands and inactivate traces of proteases. The membranes are then centrifuged and washed with buffer A twice. The pellet is resuspended in buffer A to give a protein concentration (Bradford, Anal. Biochem. 72, 248 1976) of 0.1–0.2 mg/ml and frozen in liquid $N_2$ before storage at −70° C.

B. Radioligand Binding Assay. A radioligand binding assay is conducted according to the procedure of Simon et al., supra. One of the following $P2Y_1$ receptor agonist radioligands is used in the binding assay: [$^{35}$S]3'-deoxyadenosine 5'-O-(1-thio)triphosphate ([$^{35}$S]dATPαS; 1400 Ci/mmol) or [$^3$H]UTP (14 Ci/mmol). Preliminary radioligand binding assays are conducted to identify total and nonspecific binding of the radioligand to the sample. For the specific radioligand binding assay results to have validity, nonspecific binding of radioligand should not exceed about 30% of radioligand total binding to the samples. Preliminary radioligand binding assays are also conducted to determine the concentration of radioligand which is sufficient to saturate all the available ligand binding sites on the cells. Specific binding of the radioligand to the receptor is then determined in the absence or presence of unlabelled candidate drug. Aliquots (0.5 ml final volume) of freeze-thawed membrane fraction containing 5–10 μg protein in buffer A are incubated with drug at a concentration in the range of $10^{-11}$–$10^{-4}$M and a saturation concentration of radioligand. The assay is terminated by rapid filtration through GF/C glass fibre filters (pre-soaked in 20 mM sodium pyrophosphate) and the filters are immediately washed with 3×5 ml of iced 50 mM Tris/HCl (pH 7.4) on a Millipore vacuum manifold. Filters are dried under an infra-red lamp and their radioactivity is determined using Optiphase "HiSafe" II (LKB) scintillant, at a counting efficiency routinely of 95% for $^{35}$S and 60% for $^3$H.

C. Results. The extent of the displacement of the radioactive ligand from the receptor by the drug candidate demonstrates the effectiveness of the drug candidate as a competitive inhibitor of ligand binding to the $P2Y_1$- purinoceptor. Effective inhibitors may then be tested for antagonism using the HLMC histamine release assay of Example 7.

EXAMPLE 9

Effect of Selective P2X-Purinoceptor Antagonist on Histamine Release from Human Lung Mast Cells The procedure of Example 2 was followed, except that HLMC were preincubated with the selective P2X-purinoceptor antagonist pyridzalphosphate-6-azophenyl-2', 4'-disulfonic acid or PPADS (Lambert et al., *Eur. J. Pharmacol.* 217:217–219, 1992). In four experiments, anti-IgE-induced control release of 11.2±5.3% was enhanced by ATP ($10^{4-}$M) to 15.7±7.1%. Preincubation of HLMC in PPADS ($10^{4-}$M) for fifteen minutes prior to addition of ATP ($10^{4-}$M), produced no significant modulation of the ATP effect (16.1±5.9% release).

EXAMPLE 10

P2-Purinoceptor Expression in HLMC

The following experiments demonstrate that ILMC express mRNA for both $P2Y_1$- and $P2Y_2$-purinoceptor, but not for $P2X_7/P2Z$, the purinoceptor reported to mediate histamine release from rodent mast cells, and not for $P2Y_7$, a purinoceptor found in human cell systems.

A. RNA Extraction and PCR

HLMC were challenged with either buffer or anti-IgE for two hours. Total cellular RNA (tcRNA) was then isolated from the HLMC with purity ≧90% using a modified phenol-chloroform extraction technique adapted from Chomczynski and Sacchi, *Anal. Biochem.* 162(1):156–159 (1987). Likewise, for positive controls, whole blood was processed by Ficoll-Hypaque gradient centrifugation to obtain peripheral blood mononuclear cells (Jaffe et al., *Am. J. Respir. Cell. Mol. Biol.* 13:665–675 (1995); Jaffe et al., *Am. J. Respir. Cell. Mol. Biol.* 15:473–481 (1996)) and cells similarly treated for tcRNA. Purified mast cell tcRNA was treated with 10 units Heparinase-I (Sigma Co., St. Louis, Mo.) at room temperature for 2 hours to neutralize the inhibitory effects of mast cell heparin on RT-PCR reactions (Tsai et al., *Am. J. Pathol.* 146:335–343 (1995)). cDNA was synthesized from 1 mg tcRNA using oligo (dT) primers and the murine Moloney leukemia virus reverse transcriptase (Life Technologies, Inc., Grand Island, N.Y.) at 37° C. for 1 hour in the presence of 20 units RNasin with 10 nM each of deoxynucleotide triphosphate (Promega Corporation, Madison, Wis.). Oligonucleotide probes specific for the following were synthesized: $P2Y_1$-, $P2Y_2$-, $P2Y_7$- and $P2X_7/P2Z$-purinoceptors; glyceraldehyde-3-phosphate dehydrogenase (GAPDH). Polymerase chain reaction (PCR) was performed using 1 unit Taq DNA polymerase (Life Technologies, Inc., Grand Island, N.Y.) for 30 cycles (30 seconds at 94° etc., 30 seconds at 60° etc., 60 seconds at 72° etc.) followed by an additional product extension step (72° etc. for 5 minutes) using a programmable thermal cycler (GeneAmp 9600, Perkin Elmer, Foster City, Calif.). PCR products were separated using agarose gel electrophoresis and visualized by ethidium bromide staining using a digital image analysis system (Gel Doc 1000, Bio-Rad Laboratories, Hercules, Calif.). Amplified PCR products were 370 base pairs for $P2Y_1$, 197 base pairs for $P2Y_2$, 322 base pairs for $P2Y_7$, 203 base pairs for $P2X_7/P2Z$, and 228 base pairs for GAPDH.

B. Results

In 5/5 experiments, HLMC expressed transcripts for $P2Y_1$-purinoceptor and in 3/3 experiments for $P2Y_2$-purinoceptor (FIG. 5). $P2Y_7$-purinoceptor, found in human cell systems, was undetected in 4/5 and faintly expressed in 1/5 (FIG. 5). GAPDH signal was readily detected in all cell samples at 20 cycles of PCR (FIG. 5). $P2X_7/P2Z$-purinoceptor expression was not detected in 5/5 purified HLMC preparations (FIG. 6), although GAPDH signal was readily detected in all cell samples at 20 cylces of PCR (data not shown).

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indication the scope of the invention.

What is claimed is:

1. A method for selecting compounds useful for inhibiting histamine release from stimulated human mast cells comprising:
   contacting stimulated human mast cells with a candidate compound which is an inhibitor of ATP binding to a P2Y-purinoceptor; and
   assaying said cells for release of histamine.

2. The method according to claim 1 wherein the compound is an inhibitor of ATP binding to the $P2Y_1$-purinoceptor or $P2Y_2$-purinoceptor.

3. The method according to claim 2 wherein the stimulated mast cells comprise immunologically stimulated mast cells.

4. The method according to claim 3 wherein the immunologically stimulated mast cells comprise lung mast cells.

5. A method for determining, in vitro, the effectiveness of an inhibits of ATP binding to a P2Y-purinoceptor as a candidate agent for the treatment of a human subject for a disorder characterized by undesirable release of histamine from stimulated mast cells, the method comprising:
   forming a mixture comprising the agent, a P2Y-purinoceptor ligand and a reagent comprising a P2Y-purinoceptor; and
   assaying the mixture for the inhibition of ligand binding to said receptor by the agent.

6. The method according to claim 5 wherein the reagent comprises the $P2Y_1$-purinoceptor, and the ligand is a $P2Y_1$-purinoceptor ligand, or the reagent comprises the $P2Y_2$-purinoceptor, and the ligand is a $P2Y_2$-purinoceptor ligand.

7. The method according to claim 6 wherein the reagent comprises human mast cells.

8. The method according to claim 7 wherein the reagent comprises lung mast cells.

9. The method according to claim 8 wherein the $P2Y_1$ or $P2Y_2$-purinoceptor ligand is a radiolabeled ligand.

10. The method according to claim 9 wherein the radiolabeled ligand is [$^{35}$S]3'-deoxyadenosine 5'-O-(1-thio) triphosphate or [$^3$H]uridine 5'-triphosphate.

11. The method according to claim 5 wherein the disorder is asthma.

* * * * *